United States Patent
He et al.

(10) Patent No.: US 7,269,245 B2
(45) Date of Patent: Sep. 11, 2007

(54) COMBINATORIAL SCREENING SYSTEM AND X-RAY DIFFRACTION AND RAMAN SPECTROSCOPY

(75) Inventors: Bob Baoping He, Madison, WI (US); Christopher S. Frampton, Barton on Sea (GB); Frank W. Burgäzy, Jockgrim (DE)

(73) Assignee: Bruker AXS, Inc., Madison, WI (US)

( * ) Notice: Subject to any disclaimer, the term of this patent is extended or adjusted under 35 U.S.C. 154(b) by 16 days.

(21) Appl. No.: 11/186,390

(22) Filed: Jul. 21, 2005

(65) Prior Publication Data

US 2006/0023837 A1 Feb. 2, 2006

Related U.S. Application Data

(60) Provisional application No. 60/592,713, filed on Jul. 30, 2004.

(51) Int. Cl.
*G01N 23/207* (2006.01)
*G01J 3/44* (2006.01)
(52) U.S. Cl. .......................... 378/71; 378/70; 378/73; 378/79; 378/81; 356/301
(58) Field of Classification Search ................. 378/71, 378/73, 76, 79, 80, 81, 70; 356/301
See application file for complete search history.

(56) References Cited

U.S. PATENT DOCUMENTS

| | | | | |
|---|---|---|---|---|
| 5,359,640 A | * | 10/1994 | Fink et al. | 378/79 |
| 6,459,763 B1 | * | 10/2002 | Koinuma et al. | 378/71 |
| 6,507,636 B1 | * | 1/2003 | Lehmann | 378/79 |
| 6,678,347 B1 | * | 1/2004 | Kozaczek et al. | 378/75 |
| 6,718,008 B1 | * | 4/2004 | He et al. | 378/71 |
| 6,807,251 B2 | * | 10/2004 | Okanda et al. | 378/71 |
| 6,836,532 B2 | * | 12/2004 | Durst et al. | 378/73 |
| 6,859,520 B2 | * | 2/2005 | He et al. | 378/79 |
| 2002/0067800 A1 | * | 6/2002 | Newman et al. | 378/73 |
| 2003/0124028 A1 | | 7/2003 | Carlson et al. | |

FOREIGN PATENT DOCUMENTS

EP    1357377 B1    10/2003

OTHER PUBLICATIONS

Shaofeng Ran et al., Review of Scientific Instruments 74, 3087-3092 (2003).*
Kohji Tashiro et al., Journal of Polymer Science: Part B: Polymer Physics, vol. 40, 495-506 (2002).*
G. K. Bryant et al., Review of Scientific Instruments 69, 2114-2117 (1998).*

* cited by examiner

*Primary Examiner*—Allen C. Ho
(74) *Attorney, Agent, or Firm*—The Law Offices of Paul E. Kudirka

(57) ABSTRACT

A sample analysis system makes use of both X-ray diffraction analysis and Raman spectroscopy of a sample. The sample is part of a sample library that is mounted on an XYZ stage that allows each sample to be examined in turn, as the XYZ stage is moved to position successive samples to a sample location. The system components may be mounted on a goniometer to allow their repositioning. A video system may be used for optical examination of the sample, and a knife edge may be used to prevent X-ray radiation from reaching a sample adjacent to the sample positioned at the sample location. A controller may be used to automatically control the operation of the analysis components and the movement of the sample holder to as to allow automated analysis of all of the samples in the sample holder.

20 Claims, 4 Drawing Sheets

COMBINATORIAL SCREENING SYSTEM AND X-RAY DIFFRACTION AND RAMAN SPECTROSCOPY

CROSS-REFERENCE TO RELATED APPLICATION

This application takes priority from U.S. Provisional Patent Application Ser. No. 60/592,713, filed Jul. 30, 2004.

FIELD OF THE INVENTION

The present invention relates generally to analysis for combinatorial chemistry applications and, more specifically, to the use of a multi-faceted screening system for doing combinatorial analysis.

BACKGROUND OF THE INVENTION

Combinatorial chemistry refers to techniques to collect, test, and store the resulting data for a material library containing tens, hundreds or even thousands of different materials or compounds. Combinatorial investigations require rapid screening techniques to test and evaluate variations of composition, structure and property within a material library. Screening may be done by different techniques. X-ray diffraction is one suitable screening technique, because abundant information on the atomic arrangement of the sample can be revealed from the diffraction pattern. A different screening technique is Raman spectroscopy, which may be used to measure the characteristic vibration frequencies determined by the chemical composition and chemical bond. Whichever screening technique is used, the combinatorial analysis involves sampling a number of different samples typically arranged adjacent to each other on a sample holder. Sample data is collected for all the samples in the sample array, and used collectively as part of the analysis.

SUMMARY OF THE INVENTION

In accordance with the present invention, a combinatorial screening system uses a coordinated set of sample analysis techniques to provide a robust set of sample data for doing the material characterization of samples in a sample library. The system is arranged so that an X-ray diffraction analysis component and a Raman spectroscopy component can both extract data from a sample under test. A video microscope may be used for positioning of the sample under test, and may also collect data for use in an analysis of the sample.

The sample library may be located on an XYZ stage that allows adjustment of the position of the sample library in three dimensions. A computer controller can be provided to allow automated sample positioning and data collection. When used for sample positioning, the controller controls the movement of the XYZ stage to place a particular sample under test in the desired position. The analysis may also be conducted automatically by the controller, which could initiate each of the analysis techniques and coordinate the data collection and data processing. When a sample of interest is properly positioned, the analysis components are operated. The Raman probe is used to collect inelastically scatted photons from illumination of the sample with a laser. X-ray diffraction data is gathered by illuminating the sample under test with an X-ray beam, and detecting the diffracted X-ray energy with an X-ray detector. A laser video system uses a laser to illuminate the sample under test, and a video microscope to collect video images of the sample. Once analysis of the sample under test is complete, the XYZ stage is adjusted to position a new sample of the library in the appropriate position.

In one embodiment of the invention, the Raman probe receives scattered light from the sample under test along a direction that is at an acute angle relative to the upper surface of the sample library. A laser is also at an acute angle relative to the sample library upper surface. This laser may be used in conjunction with the video microscope for illuminating the sample under test, and using the video image to make positioning adjustments and/or to collect visual data regarding the sample. With proper wavelength selection, the same laser may also be used to initiate the Raman scattering for the Raman probe, although the Raman probe may also use an exclusive laser source.

In an alternative embodiment of the invention, a knife edge is provided for use with X-ray diffraction screening. The knife edge may be positioned above the sample under test while it is being illuminated with X-rays. Since the X-ray source delivers X-ray energy along a direction that is at an acute angle relative to an upper surface of the sample library, the knife edge may thereby block X-ray energy from the X-ray source from reaching any adjacent samples, which could otherwise cause cross-contamination. In one version of this embodiment, the knife edge may be attached to the Raman probe, so that the two components move together. When the knife edge is positioned directly above the sample under test, the system is well arranged for X-ray diffraction analysis. The Raman probe and knife edge may then be moved together so that the knife edge is no longer above the sample under test, but so that the Raman probe is positioned above the sample under test. In this position, the system is well arranged for analysis by Raman spectroscopy. A third position of the knife edge/Raman probe combination could also be used in which both components are moved away from an area above the sample under test. If the video microscope was positioned above the sample under test at a position higher than that which might be occupied by the knife edge or Raman probe, the movement of those two components away from the region above the sample under test removes any visual obstruction to the video microscope. Visual data from the sample under test can then be collected, and used for sample analysis or sample positioning as necessary.

In yet another embodiment, the X-ray source and optics, the Raman probe and the laser video assembly can all be made to move in unison. For example, all three of these components can be connected to the inner circle of a goniometer which, when rotated, thereby results in the rotation of all of these components. This allows the components to have a fixed angular relationship relative to one another. It also allows the components to be give the same position and orientation relative to a sample under test when their respective data is collected.

BRIEF DESCRIPTION OF THE DRAWINGS

The above and further advantages of the invention may be better understood by referring to the following description in conjunction with the accompanying drawings in which.

DETAILED DESCRIPTION

Figure 1:
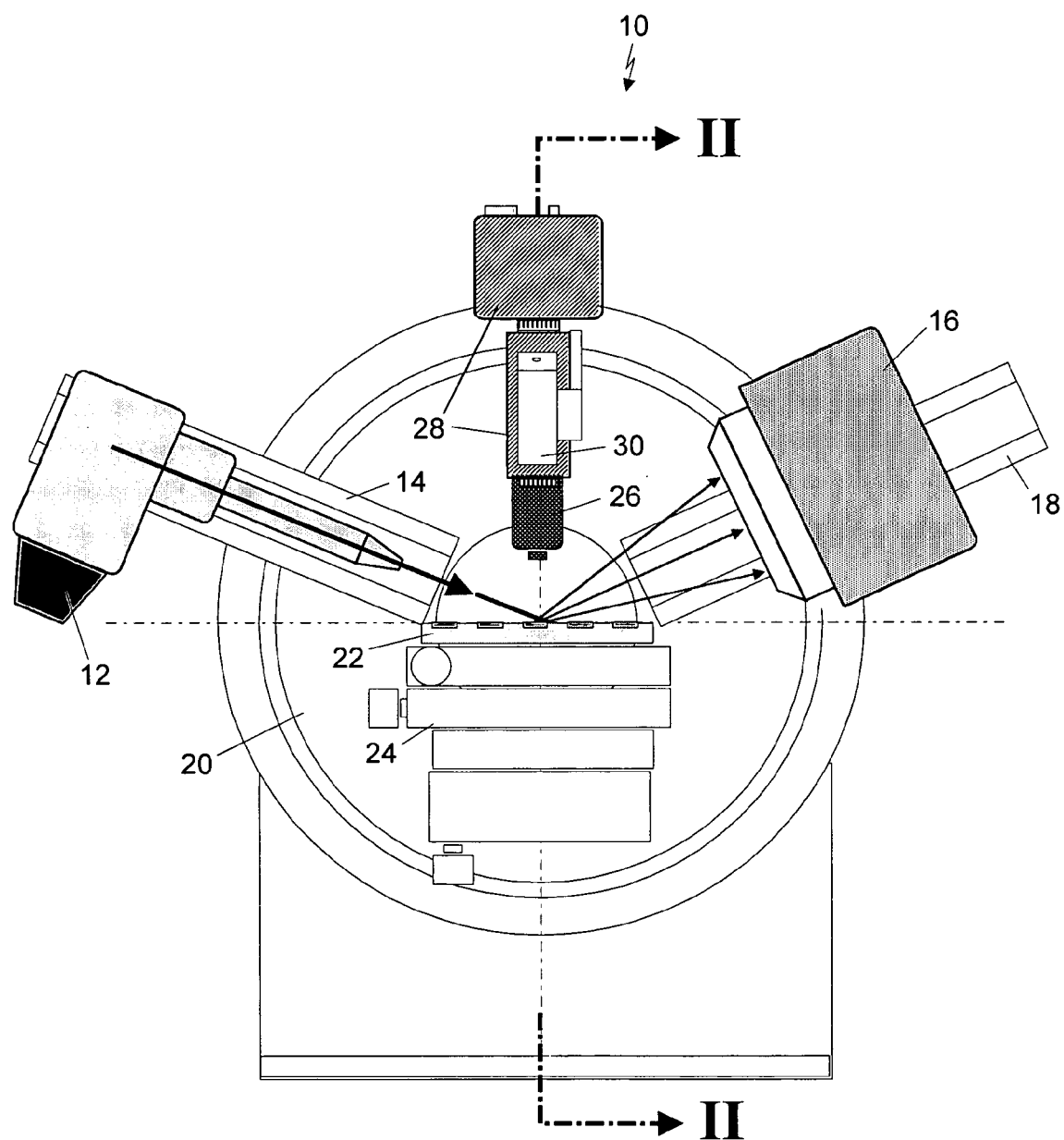
FIG. 1 is a schematic front view of an analysis system according to the present invention.

FIG. 1 is an illustration of the front view of a system consisting of an analysis system 10 that includes an X-ray diffractometer, Raman spectrometer and video microscope. In the system, the x-ray source and optics 12 are mounted on a dovetail track, referred to herein as $\theta_1$ track 14. A two-dimensional X-ray detector 16 is mounted on another dovetail track, referred to herein as $\theta_2$ track 18. $\theta_1$ track 14 is mounted to the inner circle of goniometer 20, while the $\theta_2$ track 18 is mounted on the outer circle of the goniometer. The sample library 22 is placed on an XYZ translation stage 24. The Raman probe 26, the video microscope 28 and the laser 30 are mounted on the stationary part of the goniometer 20.

The system shown in FIG. 1 is capable of collecting analytical data from a sample under test using several different techniques. The Raman probe 26 is located above the sample, and uses a laser source that delivers photonic energy to the sample, and a collection device that detects the Raman scattered photon energy. As known in the art, the Raman effect arises from inelastic scattering of photons by a solid, liquid, or gas. This effect can be used in chemical analysis because it gives rise to a unique spectrum for each compound. The Raman probe 26 may be of a known type, and filters out the photon energy from Rayleigh scattering, determining a Raman signal based on the wavelength of the photons that result from the Raman scattering. This signal gives information about the molecular structure of the sample material, and is stored and used for subsequent analysis, either alone or in conjunction with the data from the other analytical techniques.

X-ray diffraction analysis is also known in the art and, like Raman spectroscopy, is non-destructive. X-ray diffraction also gives information regarding the molecular structure of the sample material. The X-ray source and optics 12 shown in FIG. 1 operate together to deliver a properly focused X-ray beam to a sample under test. X-ray energy is diffracted from the sample in the direction of two-dimensional X-ray detector 16 where a diffraction pattern is detected that is indicative of the molecular structure of the sample. The detector output signal is then stored and used for subsequent analysis, alone or in conjunction with the data from the other analytical techniques.

A video microscope 28 may also be used in conjunction with a laser 30 to accumulate video data of the sample under test. The laser is used to illuminate the sample, while a visual image of the sample is collected by the microscope. This image data is recorded and used for analyzing the structure of the sample, either alone or in conjunction with the results of the other analytical techniques. The image data is also used for alignment of the sample support to ensure that the sample under test is positioned at the proper location.

Figure 2:
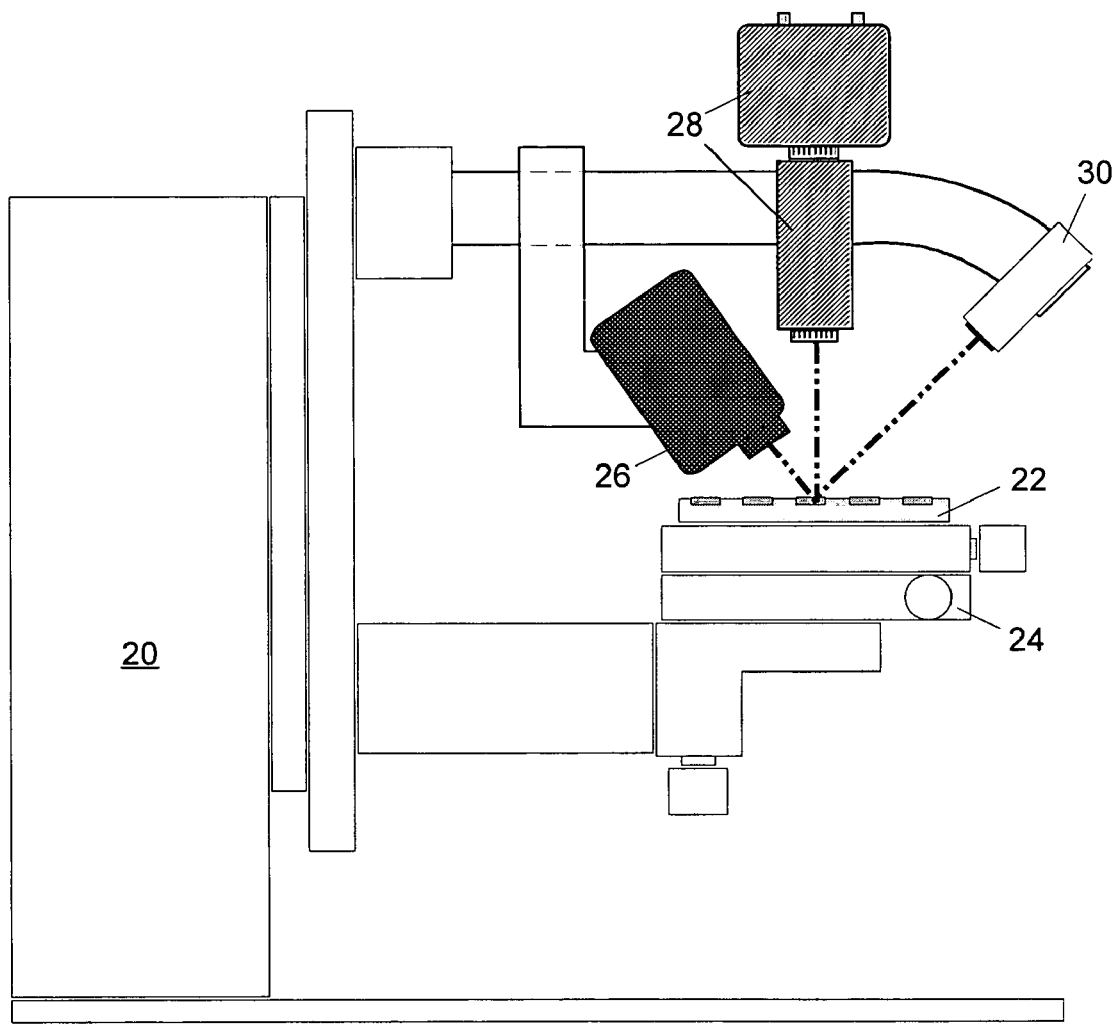
FIG. 2 is a schematic side view of the analysis system of FIG. 1.

FIG. 2 is a schematic, cross-sectional side view taken along line II-II of FIG. 1. FIG. 2 shows the space relationship between the Raman probe 26, the video microscope 28 and the laser 30. For clarity, a number of the other system components, such as the X-ray source and optics 12 and the X-ray detector 16, are not shown in this figure. The sample library 22 is shown located on XYZ translation stage 24. As shown, the laser 30 is positioned to illuminate the sample under test, while not interfering with the location of the video microscope 28 or the Raman probe 26. As mentioned above, the combination of the laser and video microscope may be used for sample alignment, and the details of such a laser-video system may be found in U.S. Pat. No. 5,359,640, the substance of which is incorporated herein by reference. The laser source for the Raman probe 26 may be part of the probe or, alternatively, the laser 30 may function as the laser source for both the video microscope 28 and the Raman probe 26. In such a case, the wavelength of the laser would have to be correctly chosen to provide proper operation of both components. This would eliminate the need for a second laser.

The laser beam and optical axis of the microscope intercept at the instrument center so the sample position can be determined by the laser spot position on the sample image. The sample positioning, changing of the sample, operation of the screening components and data collection may all be done under computer control. A computer controller may use video data to adjust motors connected to the XYZ stage so as to position a desired sample at the optimum sample position. The distance between the surface of the library cell and the instrument center is calculated from the laser spot position, and the sample height may be adjusted to locate the sample surface into the instrument center. Once a sample is in the proper position, the controller may initiate scans by any or all of the Raman probe, the X-ray diffraction components and the video components, the detected data from which is processed and/or stored for post processing. After a given sample is analyzed, the controller would then adjust the XYZ stage 24 to move the sample library 22 so that the next sample of interest was positioned at the desired sample location (typically the instrument center), and would again initiate the analysis procedure. This process would be repeated for each sample of the library to be analyzed.

Figure 3:
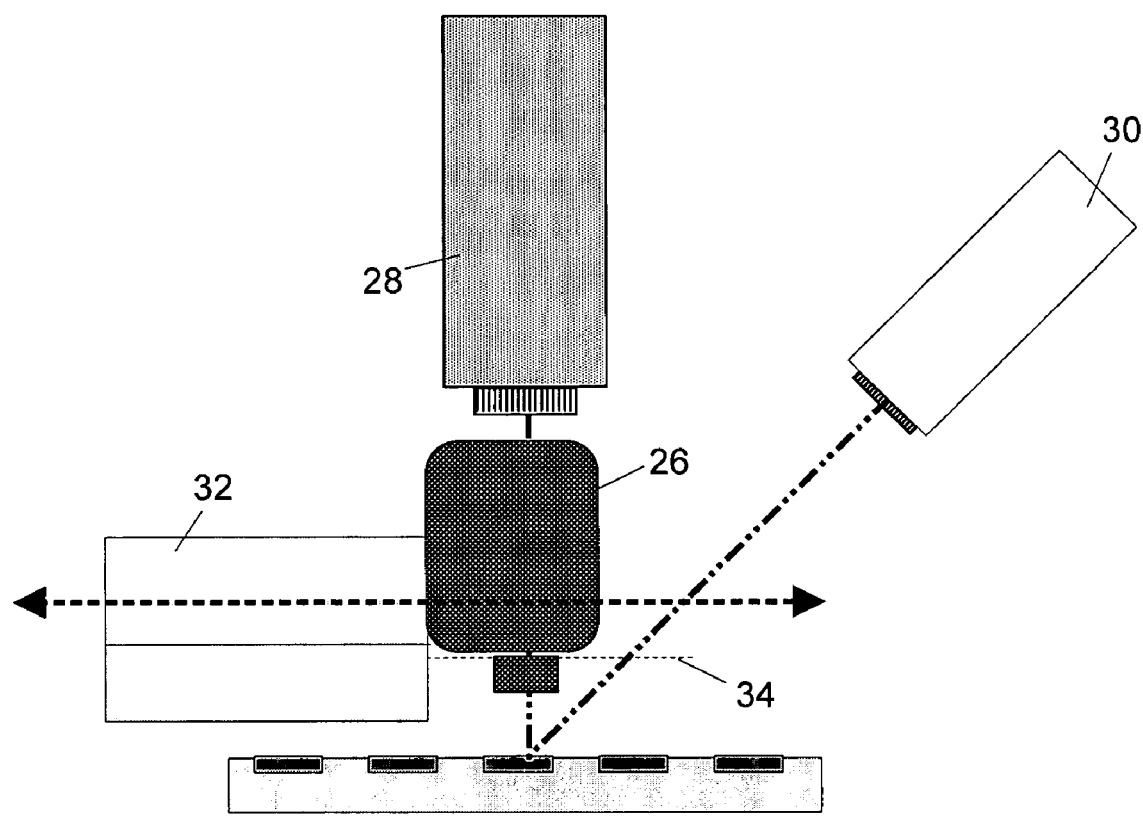
FIG. 3 is a schematic front view of some of the components of an alternative embodiment of the invention in which a Raman probe and a knife edge move together relative to a sample library.

FIG. 3 shows an alternative arrangement of the invention in which the Raman probe 26 and a knife-edge 32 are mounted on a common translation stage 34. The details of a knife-edge such as that used herein may be found in U.S. Pat. No. 6,718,008, the substance of which is incorporated herein by reference. The translation stage 34 has at least three positions: one for Raman spectroscopy; one for X-ray diffraction; and one for video image analysis. When the Raman probe 26 is positioned above a sample located at the instrument center, a Raman spectrum is collected. When the knife-edge 32 is positioned above a sample located at the instrument center, an X-ray diffraction pattern may be measured, with the knife-edge 32 providing the necessary shielding of X-ray energy that might otherwise reach an adjacent sample and result in cross-contamination. When the Raman probe 26 and the knife-edge 32 are both moved away from the sample, the video imaging system 28 has an unobstructed view of the top surface of the sample, allowing a video image to be collected. As with all of the embodiments of the invention, the movement of all the system components may be automated and controlled by a controller to allow an entire sample library to be investigated without user intervention.

Figure 4:
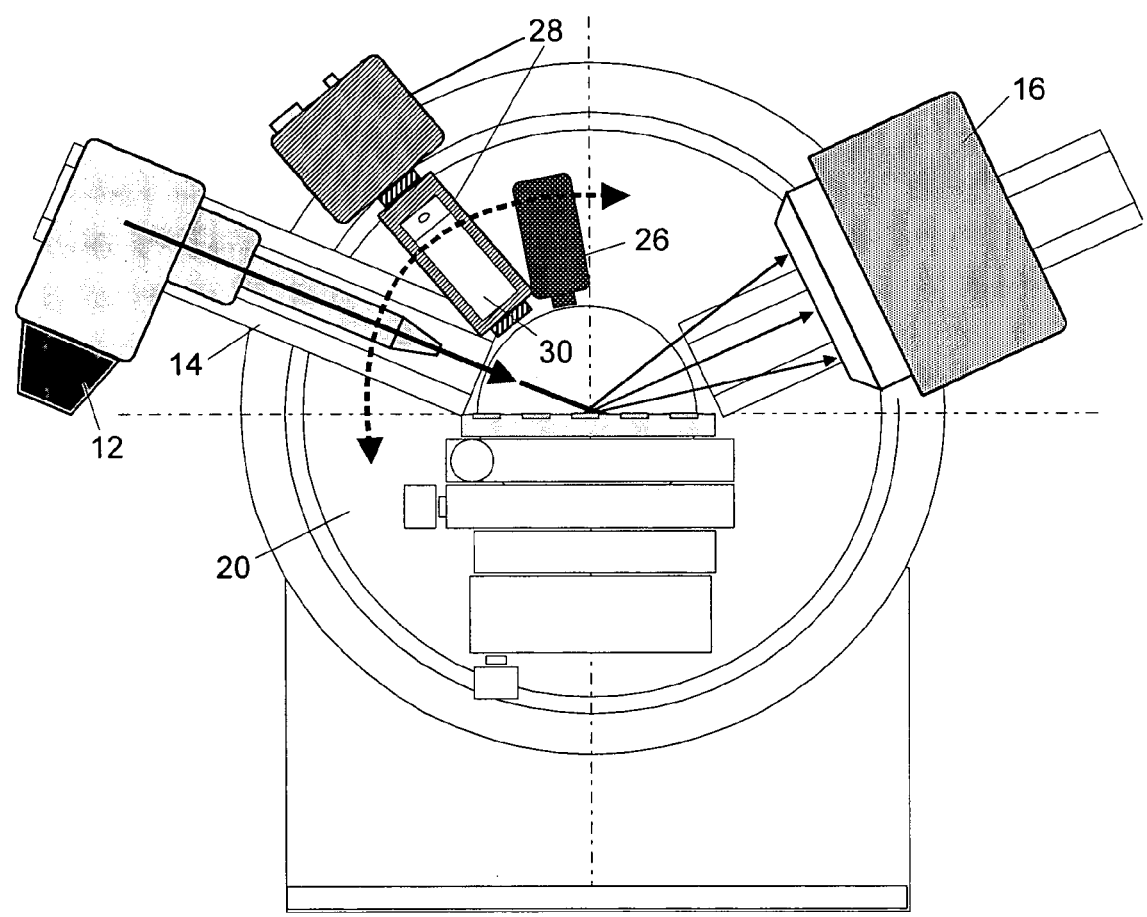
FIG. 4 is a schematic front view of another alternative embodiment of the invention in which several components are connected to the inner circle of a goniometer.

In FIG. 4 is shown another alternative configuration of the present invention. In this configuration, all three of the X-ray source/optics 12, the laser/video assembly 28, 30 and the Raman probe 26 are attached to the inner circle of the goniometer 20 (the x-ray source/optics 12 is attached via the dovetail track 14). In this arrangement, movement of the inner circle can be used to position each of the components relative to the sample library 22. For example, by rotating the inner circle, the laser/video components can be moved to a position perpendicular to the sample so that sample alignment or imaging of the sample can be performed. Rotating the inner circle to a different position locates the Raman probe 26 directly above the sample, if Raman scattering analysis from that angle is desired. Likewise, the inner circle may be rotated to position the X-ray source/optics to a desired location relative to the sample and the detector 16 for the purposes of X-ray diffraction screening.

Having all of these components attached to the inner circle allows a single motor to be used to reposition all of them. Another advantage to this configuration is that it allows the different components to occupy the same position relative to the sample. For example, both the Raman probe 26 and the laser/video assembly 28, 30 may be positioned directly above the sample when their respective data is collected (after one is operated, the inner circle is rotated to bring the other into position). Thus, the measurements may be done from the exact same position and under the same conditions.

Each of the embodiments described herein uses Raman spectroscopy in conjunction with X-ray diffraction analysis and/or video imaging. The interaction of these techniques and multiple data analyses they provide may also be extended to other types of spectroscopy, such as infrared (IR) spectroscopy or near infrared (NIR) spectroscopy, as well as other materials characterization techniques for combinatorial screening. The multiple data may be correlated to give more valuable, and often more reliable, results and is more sensitive to the differentiation among samples in a library. The different data sets may be combined to form values representative of certain types of variations among samples. For example, a ratio between the data values of two of the collected data sets might give a parameter that was more informative than any of the data sets taken alone. Likewise, integration and differentiation among two or three of the different data can provide otherwise unavailable information. The use of such multiple techniques, and/or multiple data, in a cooperative arrangement as described herein is considered within the scope of the invention.

What is claimed is:

1. An analysis system for examining the structure of samples in a library of samples mounted in a sample holder, the system comprising:
   a movable sample support that moves the sample holder to position a sample in the library at a test location;
   an X-ray source that directs X-ray energy toward the sample;
   an X-ray detector that detects X-ray energy diffracted from the sample;
   an optical source that directs photon energy toward the sample to produce a Raman excitation of the sample;
   a Raman probe that detects photon energy scattered from the sample as a result of Raman excitation of the sample;
   a mounting system for the X-ray detector and the Raman probe that movably positions at least one of the X-ray detector and the Raman probe relative to the test location; and
   a controller that, for each sample in the sample library, controls the movable sample support, the X-ray source, the X-ray detector, the Raman probe and the mounting system to move the at least one of the X-ray detector and the Raman probe into position to make an X-ray diffraction measurement and perform the X-ray diffraction measurement on that sample and to move the at least one of the X-ray detector and the Raman probe into position to make a Raman measurement and perform the Raman measurement on that sample without reloading and realigning the sample holder in the analysis system.

2. An analysis system according to claim 1 further comprising a goniometer to which the X-ray source and X-ray detector are connected.

3. An analysis system according to claim 2 wherein the X-ray source and X-ray detector are mounted to two different circles of the goniometer.

4. An analysis system according to claim 2 wherein the X-ray source and the Raman probe are mounted to the same circle of the goniometer.

5. An analysis system according to claim 1 further comprising a video apparatus for optical examination of the sample.

6. An analysis system according to claim 1 wherein the sample support is movable in at least two perpendicular directions.

7. An analysis system according to claim 1 wherein the sample support comprises a plurality of sample locations, each of which may contain an individual sample, and wherein the sample support may be moved to change which of the samples is located at the test location.

8. An analysis system according to claim 1 further comprising a knife edge located adjacent to the sample to block X-ray energy from reaching adjacent regions of the sample holder.

9. An analysis system according to claim 1 wherein the Raman probe and the knife edge are both mounted to a common movement stage such that they move in unison.

10. An analysis system for examining the structure of samples in a library of samples mounted in a sample holder having a plurality of adjacent sample locations, the system comprising:
   an X-ray source that directs X-ray energy toward a sample;
   an X-ray detector that detects X-ray energy diffracted from the sample;
   an optical source that directs photon enemy toward the sample to produce a Raman excitation of the sample:
   a Raman probe that detects photon energy scattered from the sample as a result of Raman excitation of the sample;
   a goniometer to which the X-ray detector and the Raman probe are connected and which movably positions at least one of the X-ray detector and the Raman probe relative to the sample locations;
   a movable sample support that supports the sample holder while it is mounted in the analysis system and that is movable in at least two perpendicular directions to change which of the samples is located at a predetermined sample location; and
   a controller that, for each sample in the sample library, controls the movable sample support, the X-ray source, the X-ray detector, the Raman probe and the goniometer to move that sample to the predetermined sample location and to move the at least one of the X-ray detector and the Raman probe into position to make an X-ray diffraction measurement and perform the X-ray diffraction measurement on that sample and to move the at least one of the X-ray detector and the Raman probe into position to make a Raman measurement and perform the Raman measurement on that sample so that measurements are made with both the X-ray detector and the Raman probe without reloading and realigning the sample holder in the analysis system.

11. A method of examining the structure of samples in a library of samples mounted in a sample holder, the method comprising:
supporting the sample holder with a movable sample support;
moving the sample support to position a sample in the library at a test location;
movably positioning at least one of an X-ray detector and a Raman probe relative to the test location to perform an X-ray diffraction measurement;
directing X-ray energy toward the sample with an X-ray source;
detecting X-ray energy diffracted from the sample with the X-ray detector;
movably positioning at least one of the X-ray detector and the Raman probe relative to the test location to perform a Raman spectroscopy measurement;
inducing a Raman excitation in the sample by directing photon energy from an optical source toward the sample and detecting photon energy scattered from the sample as a result of the Raman excitation with the Raman probe; and
repeating the preceding steps for each sample in the sample library so that measurements of each sample in the sample library are made with both the X-ray detector and the Raman probe without reloading and realigning the sample holder.

12. A method according to claim 11 further comprising locating the X-ray source and X-ray detector on a goniometer.

13. A method according to claim 12 wherein the X-ray source and X-ray detector are mounted to two different circles of the goniometer.

14. A method according to claim 13 wherein the X-ray source and the Raman probe are mounted to the same circle of the goniometer.

15. A method according to claim 11 further comprising optically examining the sample with a video apparatus.

16. A method according to claim 11 wherein the sample support is movable in at least two perpendicular directions.

17. A method according to claim 11 wherein the sample holder comprises a plurality of sample locations, each of which may contain an individual sample, and wherein the method further comprising moving the sample support to change which of the samples is located at the test location.

18. A method according to claim 17 further comprising controlling the movement of sample support and operation of the X-ray source, the X-ray detector and the Raman probe with a controller so as to allow automated analysis of the samples on the sample holder.

19. A method according to claim 11 further comprising locating a knife edge adjacent to the sample to block X-ray energy from reaching adjacent regions of the sample holder.

20. A method according to claim 11 wherein the Raman probe and the knife edge are both mounted to a common movement stage such that they move in unison.

* * * * *

UNITED STATES PATENT AND TRADEMARK OFFICE
CERTIFICATE OF CORRECTION

PATENT NO.        : 7,269,245 B2                                              Page 1 of 1
APPLICATION NO.   : 11/186390
DATED             : September 11, 2007
INVENTOR(S)       : Bob Baoping He, Christopher S. Frampton and Frank W. Burgäzy It is certified that error appears in the above-identified patent and that said Letters Patent is hereby corrected as shown below:

Column 6, Claim 10
Line 41, please replace "enemy" with --energy--.

Signed and Sealed this

Thirtieth Day of December, 2008

JON W. DUDAS
*Director of the United States Patent and Trademark Office*